(12) United States Patent
Wei et al.

(10) Patent No.: US 8,951,947 B2
(45) Date of Patent: *Feb. 10, 2015

(54) MULTI-PHASE PERSONAL CLEANSING COMPOSITIONS COMPRISING A LATHERING CLEANSING PHASE AND A NON-LATHERING STRUCTURED AQUEOUS PHASE

(75) Inventors: Karl Shiqing Wei, Mason, OH (US); Edward Dewey Smith, III, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 271 days.

This patent is subject to a terminal disclaimer.

(21) Appl. No.: 11/263,749

(22) Filed: Nov. 1, 2005

(65) Prior Publication Data

US 2006/0094628 A1    May 4, 2006

Related U.S. Application Data

(63) Continuation-in-part of application No. 11/001,796, filed on Dec. 2, 2004, now abandoned.

(60) Provisional application No. 60/532,798, filed on Dec. 24, 2003, provisional application No. 60/576,199, filed on Jun. 2, 2004.

(51) Int. Cl.
| | |
|---|---|
| *C11D 17/00* | (2006.01) |
| *C11D 1/02* | (2006.01) |
| *C11D 3/20* | (2006.01) |
| *C11D 3/37* | (2006.01) |
| *A61K 8/02* | (2006.01) |
| *A61Q 19/10* | (2006.01) |
| *A61K 8/73* | (2006.01) |
| *A61Q 5/02* | (2006.01) |
| *A61K 8/81* | (2006.01) |

(52) U.S. Cl.
CPC ............... *A61K 8/0237* (2013.01); *A61K 8/02* (2013.01); *A61Q 19/10* (2013.01); *A61K 8/737* (2013.01); *A61Q 5/02* (2013.01); *A61K 8/8152* (2013.01)
USPC .......... 510/127; 510/130; 510/137; 510/138; 510/158; 510/159; 510/417; 510/488; 510/502; 510/505; 510/506

(58) Field of Classification Search
USPC ......... 510/127, 130, 137, 138, 158, 159, 417, 510/488, 502, 505, 506
See application file for complete search history.

(56) References Cited

U.S. PATENT DOCUMENTS

| | | |
|---|---|---|
| 2,020,454 A | 11/1935 | Bisbee et al. |
| 2,658,072 A | 11/1953 | Kosmin |
| 2,986,271 A | 5/1961 | Forrer |
| 3,455,440 A | 7/1969 | West |
| 3,479,429 A | 11/1969 | Morshauser et al. |
| 3,533,955 A | 10/1970 | Pader et al. |
| 3,542,256 A | 11/1970 | Waterman |
| 3,618,757 A | 11/1971 | Funkhouser |
| 3,800,998 A | 4/1974 | Gask |
| 3,850,365 A | 11/1974 | Dietrich |
| 3,899,076 A | 8/1975 | Florian |
| 3,929,678 A | 12/1975 | Laughlin et al. |
| 3,937,811 A | 2/1976 | Papantoniou et al. |
| 3,951,679 A | 4/1976 | Bernhard et al. |
| 3,980,767 A | 9/1976 | Chown et al. |
| 4,159,028 A | 6/1979 | Barker et al. |
| 4,263,363 A | 4/1981 | Buck et al. |
| 4,335,103 A | 6/1982 | Baker et al. |
| 4,379,753 A | 4/1983 | Bolich, Jr. |
| 4,425,322 A | 1/1984 | Harvey et al. |
| 4,518,578 A | 5/1985 | Hayes et al. |
| D292,879 S | 11/1987 | Smith |
| 4,818,575 A | 4/1989 | Hirata et al. |
| 4,966,205 A | 10/1990 | Tanaka |
| 4,980,155 A | 12/1990 | Shah et al. |
| 5,002,680 A | 3/1991 | Schmidt et al. |
| 5,059,414 A | 10/1991 | Dallal et al. |
| 5,223,315 A | 6/1993 | Katsura et al. |
| 5,228,189 A | 7/1993 | Driller et al. |
| 5,304,334 A | 4/1994 | Lahanas et al. |
| 5,393,450 A | 2/1995 | Shana'a et al. |
| 5,455,035 A | 10/1995 | Guerrero et al. |
| 5,487,168 A | 1/1996 | Geiner et al. |
| 5,540,853 A | 7/1996 | Trinh et al. |
| 5,556,628 A | 9/1996 | Derian et al. |
| 5,578,299 A | 11/1996 | Starch |
| 5,612,307 A | 3/1997 | Chambers et al. |

(Continued)

FOREIGN PATENT DOCUMENTS

| | | |
|---|---|---|
| CA | 2246316 | 6/1998 |
| DE | 19650952 1 A | 6/1998 |
| DE | 198 54 086 A1 | 5/2000 |
| EP | 0 078138 A2 | 5/1983 |
| EP | 0 331617 B1 | 4/1992 |
| EP | 1 108421 A2 | 6/2001 |
| EP | 1 005849 B1 | 9/2001 |
| EP | 1064918 B1 | 9/2002 |
| EP | 0 907345 B1 | 5/2003 |
| GB | 1277324 A | 6/1972 |
| JP | 2000229817 A | 8/2000 |
| JP | 2002-128639 A | 5/2002 |
| JP | 2002-138010 A | 5/2002 |
| KR | 2003-0045037 | 6/2003 |

(Continued)

OTHER PUBLICATIONS

International Search Report PCT/US2004/043328 mailed May 18, 2005 including the Written Opinion of the International Searching Authority, 12 pages.

(Continued)

*Primary Examiner* — Gregory R Delcotto

(57) ABSTRACT

The present invention relates to multi-phase personal cleansing compositions containing a lathering cleansing phase and a separate non-lathering structured aqueous phase wherein the two phases are packaged in physical contact while remaining stable over time.

37 Claims, No Drawings

(56) References Cited

U.S. PATENT DOCUMENTS

| | | |
|---|---|---|
| 5,632,420 A | 5/1997 | Lohrman et al. |
| 5,635,171 A | 6/1997 | Nadaud et al. |
| 5,661,189 A | 8/1997 | Grievson et al. |
| 5,687,779 A | 11/1997 | Andersson et al. |
| 5,716,920 A | 2/1998 | Glenn et al. |
| 5,851,978 A | 12/1998 | Shana'a |
| 5,873,494 A | 2/1999 | Dallas, Jr. |
| 5,914,117 A | 6/1999 | Lavaud |
| 5,925,603 A | 7/1999 | D'Angelo |
| 5,929,019 A | 7/1999 | Puvvada et al. |
| 5,947,335 A | 9/1999 | Milio et al. |
| 5,952,286 A | 9/1999 | Puvvada et al. |
| 5,954,213 A | 9/1999 | Gerhart et al. |
| 5,965,500 A | 10/1999 | Puvvada |
| 5,965,501 A | 10/1999 | Rattinger et al. |
| 5,972,361 A | 10/1999 | Fowler et al. |
| D426,158 S | 6/2000 | Flurer et al. |
| 6,174,845 B1 | 1/2001 | Rattinger et al. |
| 6,176,391 B1 | 1/2001 | Rehkemper et al. |
| 6,176,395 B1 | 1/2001 | Abbott et al. |
| 6,190,648 B1 | 2/2001 | Kouzu et al. |
| 6,194,364 B1 | 2/2001 | Glenn, Jr. |
| D438,460 S | 3/2001 | Hammond |
| D439,165 S | 3/2001 | Erckelbout et al. |
| 6,213,166 B1 | 4/2001 | Thibiant et al. |
| D441,645 S | 5/2001 | Longhurst |
| 6,232,496 B1 | 5/2001 | Carr et al. |
| 6,245,323 B1 | 6/2001 | Christie et al. |
| 6,245,344 B1 | 6/2001 | Thibiant et al. |
| 6,268,322 B1 | 7/2001 | St. Lewis et al. |
| 6,306,806 B1 | 10/2001 | St. Lewis et al. |
| 6,335,312 B1 | 1/2002 | Coffindaffer et al. |
| 6,340,723 B1 | 1/2002 | Nita et al. |
| 6,358,909 B1 * | 3/2002 | Ochomogo et al. .......... 510/417 |
| D455,655 S | 4/2002 | Bunce |
| 6,367,519 B2 | 4/2002 | Thibiant et al. |
| 6,383,999 B1 | 5/2002 | Coyle et al. |
| 6,385,992 B1 | 5/2002 | Flore, Jr. |
| 6,394,323 B2 | 5/2002 | McClean et al. |
| 6,419,783 B1 | 7/2002 | Rainey et al. |
| 6,426,326 B1 | 7/2002 | Mitra et al. |
| 6,429,177 B1 * | 8/2002 | Williams et al. ............... 510/130 |
| 6,486,106 B1 * | 11/2002 | Charlton et al. ............... 510/130 |
| 6,495,498 B2 | 12/2002 | Niemiec et al. |
| 6,506,391 B1 | 1/2003 | Biatry |
| 6,517,939 B1 | 2/2003 | Ramin et al. |
| 6,521,216 B1 | 2/2003 | Glandorf et al. |
| 6,534,456 B2 | 3/2003 | Hayward et al. |
| 6,534,457 B2 | 3/2003 | Mitra |
| 6,534,458 B1 | 3/2003 | Kakizawa et al. |
| 6,547,063 B1 | 4/2003 | Zaveri et al. |
| 6,555,509 B2 | 4/2003 | Abbas et al. |
| 6,564,978 B1 | 5/2003 | Safian et al. |
| 6,574,985 B2 | 6/2003 | Fiore, Jr. |
| 6,589,509 B2 | 7/2003 | Keller et al. |
| 6,652,134 B2 | 11/2003 | Lloyd |
| 6,663,855 B2 | 12/2003 | Frechet et al. |
| 6,673,371 B2 | 1/2004 | Brown et al. |
| 6,673,755 B2 | 1/2004 | Wei et al. |
| D486,395 S | 2/2004 | Faure et al. |
| D486,398 S | 2/2004 | Lovell et al. |
| 6,691,394 B1 | 2/2004 | McClean |
| 6,695,510 B1 | 2/2004 | Look et al. |
| 6,782,307 B2 | 8/2004 | Wilmott et al. |
| 6,903,057 B1 * | 6/2005 | Tsaur ........................... 510/130 |
| 6,919,303 B2 | 7/2005 | Pham et al. |
| 6,924,256 B2 | 8/2005 | Massaro et al. |
| 7,143,893 B2 | 12/2006 | Kelly |
| 7,144,542 B2 | 12/2006 | Holzer et al. |
| 7,273,837 B2 | 9/2007 | Boutique et al. |
| 7,511,003 B2 | 3/2009 | Focht et al. |
| 7,524,807 B2 | 4/2009 | Clapp et al. |
| 7,666,825 B2 | 2/2010 | Wagner et al. |
| 7,820,609 B2 | 10/2010 | Soffin et al. |
| 8,084,407 B2 | 12/2011 | Soffin et al. |
| 8,088,721 B2 | 1/2012 | Soffin et al. |
| 8,105,996 B2 | 1/2012 | Wei et al. |
| 8,158,566 B2 | 4/2012 | Wei |
| 2001/0036467 A1 | 11/2001 | Thibiant et al. |
| 2002/0004468 A1 | 1/2002 | Hodge et al. |
| 2002/0010110 A1 | 1/2002 | Hayward et al. |
| 2002/0022040 A1 | 2/2002 | Robinson et al. |
| 2002/0128162 A1 * | 9/2002 | Elliott et al. .................. 510/130 |
| 2003/0003069 A1 | 1/2003 | Carson et al. |
| 2003/0118540 A1 * | 6/2003 | Charlton et al. ........... 424/70.17 |
| 2003/0152540 A1 | 8/2003 | Putman et al. |
| 2003/0161852 A1 | 8/2003 | Miller et al. |
| 2003/0180246 A1 | 9/2003 | Frantz et al. |
| 2003/0181341 A1 * | 9/2003 | Yoshimi ....................... 510/156 |
| 2003/0222100 A1 | 12/2003 | Husband et al. |
| 2004/0048757 A1 | 3/2004 | Zhang et al. |
| 2004/0048758 A1 | 3/2004 | Zhang et al. |
| 2004/0057920 A1 | 3/2004 | Focht et al. |
| 2004/0091445 A1 | 5/2004 | Dykstra et al. |
| 2004/0092415 A1 | 5/2004 | Focht et al. |
| 2004/0105827 A1 | 6/2004 | Grimm et al. |
| 2004/0146475 A1 | 7/2004 | Peffly et al. |
| 2004/0158940 A1 | 8/2004 | Wells et al. |
| 2004/0180020 A1 | 9/2004 | Manelski et al. |
| 2004/0219119 A1 | 11/2004 | Wei et al. |
| 2004/0223929 A1 | 11/2004 | Clapp et al. |
| 2004/0223991 A1 | 11/2004 | Wei et al. |
| 2004/0223992 A1 | 11/2004 | Clapp et al. |
| 2004/0223993 A1 | 11/2004 | Clapp et al. |
| 2004/0232023 A1 | 11/2004 | Bansal et al. |
| 2004/0235693 A1 | 11/2004 | Wei et al. |
| 2004/0242706 A1 | 12/2004 | Wiersema et al. |
| 2004/0248748 A1 | 12/2004 | Wei et al. |
| 2004/0248749 A1 | 12/2004 | Mitra et al. |
| 2005/0003975 A1 | 1/2005 | Browne et al. |
| 2005/0020468 A1 | 1/2005 | Frantz et al. |
| 2005/0100570 A1 | 5/2005 | Wei et al. |
| 2005/0139574 A1 | 6/2005 | Simone et al. |
| 2005/0143269 A1 | 6/2005 | Wei et al. |
| 2005/0192187 A1 | 9/2005 | Wagner et al. |
| 2005/0192188 A1 | 9/2005 | Wagner et al. |
| 2005/0192189 A1 | 9/2005 | Wagner et al. |
| 2005/0238680 A1 | 10/2005 | Stella et al. |
| 2005/0249758 A1 | 11/2005 | Di Puccio Pagano |
| 2005/0269372 A1 | 12/2005 | Smith |
| 2005/0276768 A1 | 12/2005 | Wei et al. |
| 2006/0002880 A1 | 1/2006 | Peffly et al. |
| 2006/0008438 A1 | 1/2006 | Velarde et al. |
| 2006/0079419 A1 | 4/2006 | Wagner et al. |
| 2006/0079420 A1 | 4/2006 | Wagner et al. |
| 2006/0094628 A1 | 5/2006 | Wei et al. |
| 2006/0210505 A1 | 9/2006 | Clapp et al. |
| 2006/0276357 A1 | 12/2006 | Smith, III et al. |
| 2007/0137042 A1 | 6/2007 | Focht et al. |
| 2007/0141001 A1 | 6/2007 | Clapp et al. |
| 2007/0187274 A1 | 8/2007 | Dalea et al. |
| 2007/0248562 A1 | 10/2007 | Berry et al. |
| 2007/0280976 A1 | 12/2007 | Taylor et al. |
| 2010/0209374 A1 | 8/2010 | Wei et al. |
| 2011/0226272 A1 | 9/2011 | Focht et al. |

FOREIGN PATENT DOCUMENTS

| | | |
|---|---|---|
| WO | WO 90/13283 A1 | 11/1990 |
| WO | WO 94/10973 A1 | 5/1994 |
| WO | WO 97/17938 A1 | 5/1997 |
| WO | WO 98/27193 A1 | 6/1998 |
| WO | WO 98/33477 A1 | 8/1998 |
| WO | WO 99/38489 A1 | 8/1999 |
| WO | WO 99/38491 A1 | 8/1999 |
| WO | WO 00/75240 A1 | 12/2000 |
| WO | WO 01/01931 A1 | 1/2001 |
| WO | WO 01/23517 A1 | 4/2001 |
| WO | WO 01/70193 A2 | 9/2001 |
| WO | WO 01/70926 A1 | 9/2001 |
| WO | WO 02/100358 A1 | 12/2002 |
| WO | WO 03/055456 A1 | 7/2003 |
| WO | WO 03/105796 A1 | 12/2003 |
| WO | WO 2004/018609 A2 | 3/2004 |

(56) References Cited

FOREIGN PATENT DOCUMENTS

| WO | WO 2004/026276 A1 | 4/2004 |
|---|---|---|
| WO | WO 2004/050055 A1 | 6/2004 |
| WO | WO 2005/067875 A1 | 7/2005 |

OTHER PUBLICATIONS

International Search Report PCT/US2008/058556 mailed Oct. 22, 2010 including the Written Opinion of the International Searching Authority, 17 pages.

XP 002332778 "Dove All Day Moisturizing Body Wash" Online URL: http://www.ewg.org/reports/skindeep2/report.php?type=PRODUCT&id=8801874, accessed Feb. 8, 2006 (6 pages).

C.D. Vaughan, "Solubility, Effects in Product, in Package, Penetration and Preservation," Cosmetic and Toiletries, vol. 103, Oct. 1988.

Crank, Mathematics of Diffusion, $2^{nd}$ Edition, 1975, p. 63.

CTFA International Cosmetic Ingredient Dictionary, Fourth Edition, Aug. 12, 1991, pp. 12 and 80.

Household Products Database, Brand Information, "Olay Daily Renewal Moisturizing Body Wash, Calming," [Online] URL: http://householdproducts.nlm nih gov/cgi-bin/household/brands?tbl=brands&id=16003084, accessed Feb. 8, 2006 (2 pages).

Milton, Introduction to Probability and Statistics, $4^{th}$ Edition (Section 9.2: Testing Hypotheses on a Proportion), pp. 129-131, accessed Jun. 9, 2008.

J. Caelles et al., "Anionic and Cationic Compounds in Mixed Systems," Cosmetics & Toiletries, vol. 106, Apr. 1991. pp. 49-54.

C.J. van Oss, "Coacervation, Complex-Coacervation and Flocculation," J. Dispersion Science and Technology, vol. 9 (5, 6), 1988-89, p. 561-573.

D.J. Burgess, "Practical Analysis of Complex Coacervate Systems," J. Of Colloid Anti Interface Science, vol. 140, No. 1, Nov. 1990, pp. 227-238.

KOBO Brochure, "Treated Pigments" (May 2000).

\* cited by examiner

MULTI-PHASE PERSONAL CLEANSING COMPOSITIONS COMPRISING A LATHERING CLEANSING PHASE AND A NON-LATHERING STRUCTURED AQUEOUS PHASE

CROSS REFERENCE TO RELATED APPLICATIONS

This application is a continuation-in-part of U.S. application Ser. No. 11/001,796, now abandoned, filed Dec. 2, 2004, which claims the benefit of U.S. Provisional Application No. 60/532,798, filed Dec. 24, 2003 and U.S. Provisional Application No. 60/576,199, filed Jun. 2, 2004.

FIELD OF THE INVENTION

The present invention relates to multi-phase personal cleansing compositions comprising a lathering cleansing phase and a separate non-lathering structured aqueous phase wherein the two phases are packaged in physical contact while remaining stable over time.

BACKGROUND OF THE INVENTION

The ability to place a lathering cleansing phase in physical contact with a non-lathering structured aqueous phase and maintain stability for any period of time has proved to be a problem. The physical contact of a non-lathering structured aqueous phase and a lathering cleansing phase creates a situation where they are thermodynamically unstable.

One attempt at providing a non-lathering structured aqueous phase and lathering cleansing phase from a personal cleansing product while maintaining stability would be the use of dual-chamber packaging. These packages comprise separate cleansing compositions and non-lathering structured aqueous compositions, and allow for the co-dispensing of the two in a single or dual stream. The separate non-lathering structured aqueous composition and lathering cleansing compositions thus remain physically separate and stable during prolonged storage and just prior to application, but then mix during or after dispensing to provide conditioning and cleansing benefits from a physically stable system. Although such dual-chamber delivery systems provide improved cleansing benefits versus conventional systems, it is often difficult to achieve consistent and uniform performance because of the uneven dispensing ratio between the lathering cleansing phase and the non-lathering structured aqueous phase from these dual-chamber packages. Additionally, these packaging systems add considerable cost to the finished product.

Accordingly, the need still remains for stable personal cleansing compositions that provide cleansing with increased lather longevity and improved lathering characteristics, and skin benefits such as silky skin feel, improved soft skin feel, and improved smooth skin feel. It has now been found that multi-phase personal cleansing compositions comprising two phases in physical contact that remain stable over time can be formulated.

The multi-phase personal cleansing compositions of the present invention comprise a lathering cleansing phase and a non-lathering structured aqueous phase that are packaged in physical contact yet remain stable.

The compositions of the present invention further provide superior aesthetics via the multi-phased appearance and improved skin feel during and after application. It has been found that such compositions can be formulated into two separate hydrophilic phases in physical contact without compromising product lather performance and stability.

It has also been found that the multi-phase personal cleansing compositions herein can be formulated with selected skin active agents that provide improved chronic skin benefits to the skin. These compositions comprise a lathering cleansing phase containing a cleansing surfactant and at least one additional non-lathering structured aqueous phase wherein a skin active agent can be found in either phase or both phases at the same time, wherein the lathering cleansing and the non-lathering structured aqueous phase are packaged in physical contact while remaining stable over time.

SUMMARY OF THE INVENTION

The present invention is directed to a multi-phase personal cleansing composition comprising:
  (a) a first phase comprising a lathering cleansing phase comprising a surfactant and water; and
  (b) at least one additional phase comprising a non-lathering structured aqueous phase; wherein the lathering cleansing phase and the non-lathering structured aqueous phase are packaged in physical contact with one another and maintain stability.

The present invention further relates to a multi-phase personal cleansing composition comprising a lathering cleansing phase and non-lathering structured aqueous phase wherein at least one phase contains a colorant, wherein both phases are packed in a single package such that the two phases form a pattern visible to the naked eye.

The present invention further relates to a multi-phase personal cleansing composition comprising:
  a) a first phase comprising a lathering cleansing phase comprising from about 1% to about 90%, by weight of the lathering cleansing phase, of a surfactant selected from the group consisting of anionic surfactant, nonionic surfactant, zwitterionic surfactant, cationic surfactant, soap, and mixtures thereof;
  wherein the lathering cleansing phase is non-Newtonian shear thinning, has a viscosity of equal to or greater than about 3,000 cps, and/or has a yield value of at least about 0.1 Pa; and
  b) at least one additional phase comprising a separate non-lathering structured aqueous phase having a consistency value of at least about 10 poise/(1/s) and
  wherein the ratio of the lathering cleansing phase to the non-lathering structured aqueous phase is from about 10:1 to about 1:10; wherein the lathering cleansing phase and non-lathering structured aqueous phase form a pattern of stripes.

The present invention is also directed to a multi-phase personal cleansing composition comprising: (a) a first phase comprising a lathering cleansing phase comprising a surfactant and water; and (b) at least one additional phase comprising a non-lathering structured aqueous phase;
wherein at least one phase comprises a colorant; and wherein the lathering cleansing phase and the non-lathering structured aqueous phase are packaged in physical contact with one another and form a pattern.

The present invention is also directed to a method of cleansing and delivering skin benefit agents to the skin by applying to the skin a composition as described above.

DETAILED DESCRIPTION OF THE INVENTION

The multi-phase personal cleansing compositions of the present invention comprise a first phase comprising a lathering cleansing phase, and at least one separate additional phase comprising a non-lathering structured aqueous phase. The non-lathering structured aqueous phase can be hydrophilic and in a preferred embodiment the non-lathering structured aqueous phase can be a hydrophilic gelled water phase. These and other essential limitations of the compositions and methods of the present invention, as well as many of the optional ingredients suitable for use herein, are described in detail hereinafter.

By the term "multi-phased" or "multi-phase" as used herein, is meant that the lathering cleansing phase and the non-lathering structured aqueous phase herein occupy separate but distinct physical spaces inside the package in which they are stored, but are in direct contact with one another (i.e., they are not separated by a barrier and they are not emulsified or mixed to any significant degree). In one preferred embodiment of the present invention, the "multi-phase" personal cleansing compositions comprising the lathering cleansing phase and the non-lathering structured aqueous phase are present within the container as a visually distinct pattern. The pattern results from the mixing or homogenization of the "multi-phased" composition. The patterns include but are not limited to the following examples: striped, marbled, rectilinear, interrupted striped, check, mottled, veined, clustered, speckled, geometric, spotted, ribbons, helical, swirl, arrayed, variegated, textured, grooved, ridged, waved, sinusoidal, spiral, twisted, curved, cycle, streaks, striated, contoured, anisotropic, laced, weave or woven, basket weave, spotted, and tessellated. The pattern may be striped and may be relatively uniform and even across the dimension of the package. Alternatively, the striped pattern may be uneven, i.e. wavy, or may be non-uniform in dimension. The striped pattern does not need to necessarily extend across the entire dimension of the package. The size of the stripes is at least about 0.1 mm in width and 10 mm in length, preferably at least about 1 mm in width and at least 20 mm in length. The phases can form various geometric shapes, be various different colors, or include glitter or pearlescence.

The term "ambient conditions" as used herein, refers to surrounding conditions at one (1) atmosphere of pressure, 50% relative humidity, and 25° C.

The term "stable" as used herein, unless otherwise specified, refers to compositions that maintain at least two "separate" phases when sitting in physical contact at ambient conditions for a period of at least about 180 days. By "separate" is meant that there is substantially no mixing of the phases, observable to the naked eye, prior to dispensing of the composition.

The term "personal cleansing composition" as used herein, refers to compositions intended for topical application to the skin or hair.

The term "phases" as used herein, refers to a region of a composition having one average composition, as distinct from another region having a different average composition, wherein the regions are visible to the naked eye. This would not preclude the distinct regions from comprising two similar phases where one phase could comprise pigments, dyes, particles, and various optional ingredients, hence a region of a different average composition.

The phrase "substantially free of" as used herein, means that the composition comprises less than about 3%, preferably less than about 1%, more preferably less than about 0.5%, even more preferably less than about 0.25%, and most preferably less than about 0.1%, by weight of the composition, of the stated ingredient.

The personal cleansing compositions and methods of the present invention can comprise, consist of, or consist essentially of, the essential elements and limitations of the invention described herein, as well as any additional or optional ingredients, components, or limitations described herein or otherwise useful in personal cleansing compositions intended for topical application to the hair or skin.

Product Form

The personal cleansing compositions of the present invention are typically in the form of a liquid. The term "liquid" as used herein means that the composition is generally flowable to some degree. "Liquids", therefore, can include liquid, semi-liquid, cream, lotion or gel compositions intended for topical application to skin. The compositions typically exhibit a viscosity of equal to or greater than about 3,000 cps to about 1,000,000 cps, as measured by the Viscosity Method described hereinafter. In addition, the ratio of the lathering cleansing phase to the non-lathering structured aqueous phase is from about 10:1 to about 1:10.

The compositions comprise a lathering cleansing phase and a non-lathering structured aqueous phase, both of which are described in greater detail hereinafter. In a preferred embodiment of the present invention the multi-phased personal cleansing composition, the composition has at least two visually distinct phases wherein at least one phase is visually distinct from a second phase. The visually distinct phases are packaged in physical contact with one another and are stable.

The product forms contemplated for purposes of defining the compositions and methods of the present invention are rinse-off formulations, by which is meant the product is applied topically to the skin or hair and then subsequently (i.e., within minutes) rinsed away with water, or otherwise wiped off using a substrate or other suitable removal means.

Non-Lathering Structured Aqueous Phase

The non-lathering structured aqueous phase of the compositions of the present invention comprises a water structurant and water. The non-lathering structured aqueous phase can be hydrophilic and in a preferred embodiment the non-lathering structured aqueous phase is a hydrophilic gelled water phase. In addition, the non-lathering structured aqueous phase of the present invention typically comprises less than about 5%, preferably less than about 3%, and more preferably less than about 1%, by weight of the non-lathering structured aqueous phase, of a surfactant. In one embodiment of the present invention, the non-lathering structured aqueous phase is free of surfactant. The non-lathering structured aqueous phase of the personal care compositions preferably produces a Total Lather Volume of no greater than about 500 ml, more preferably no greater than about 400 ml, even more preferably no greater than about 350 ml, as measured by the Lather Volume Test described hereinafter. The non-lathering structured aqueous phase of the personal care compositions preferably produces a Flash Lather Volume of no greater than about 150 ml, preferably no greater than about 130 ml, even more preferably no greater than about 110 ml, as measured by the Lather Volume Test described hereinafter.

Preferably, the non-lathering structured aqueous phase exhibits a Yield Point of at least about 0.1 Pa, preferably at least about 1 Pa, more preferably at least about 10 Pa, as measured by the Yield Point Method described hereinafter.

Preferably, the non-lathering structured aqueous phase exhibits a Water Mobility of less than about 2.5 seconds, more preferably less than about 2 seconds, even more preferably less than about 1 second, as measured by the Water Mobility Method described hereinafter.

Preferably, the non-lathering structured aqueous phase exhibits a Correlated Haze of less than about 50% Correlated Haze, more preferably less than about 30% Correlated Haze, even more preferably less than about 20% Correlated Haze, and still more preferably less than about 10% Correlated Haze as measured by the Correlated Haze Index Method described hereafter. The non-lathering structured aqueous phase has a preferred rheology profile as defined by Consistency Value (k) and Shear Index (n). Preferred Consistency Values of the non-lathering structured aqueous phase are from about 10 to about 100,000 poise/(1/s), preferably from about 10 to about 10,000 poise/(1/s), and more preferably from about 100 to about 1,000 poise/(1/s). The Shear Index of the non-lathering structured aqueous phase typically ranges from about 0.1 to about 0.8, preferably from about 0.1 to about 0.5, and more preferably from about 0.20 to about 0.4.

The Shear Index (n) and Consistency Value (k) are well-known and accepted industry standards for reporting the viscosity profile of materials having a viscosity that is a function of an applied shear rate.

The viscosity ($\mu$) for a non-lathering structured aqueous phase can be characterized by either applying a shear rate and measuring the resultant shear stress or vice versa in a programmed manner using a rheometer, such as a TA Instruments AR2000 (TA Instruments, New Castle, Del., USA 19720). Viscosity is determined at different shear rates in the following manner. First, the non-lathering structured aqueous phase is obtained which has the composition and properties as existing in the multi-phase personal care composition. That is, the composition is processed in a similar manner such that, for example, it is crystallized at approximately the same rate, if the sample contains crystals. An aliquot of the non-lathering structured aqueous phase can be obtained prior to combining in the multiphase composition, as is common practice to those having skill in the art. Also, the non-lathering structured aqueous phase can be recovered from the multi-phase personal care composition, for example by centrifuging, pipetting, sieving, rinsing, or other means to recover the non-lathering structured aqueous phase. The AR2000 rheometer is programmed to shear the sample by ramping the stress from about 0.1 Pa to about 1,000 Pa over a 5 minute interval at 25 degrees Celsius. A 4 cm parallel plate geometry with a gap of 1 mm is common, although the gap can be increased or decreased as necessary, for example if the non-lathering structured aqueous phase contains large particles, the gap may need to be larger. A shear rate of at least 100 1/seconds is obtained in the test, or the test is repeated with a higher final stress value while maintaining the programmed rate of stress increase at about 1.25 minutes per decade of stress. These results are fitted with the following well accepted power law model. Data in the sheared region are included, by plotting the viscosity and shear rate data on a log-log plot, and utilizing only the data in the region where shear rate is ascending and viscosity is descending in steady fashion. For example, an initial plateau region at low shear stress where little flow occurs is not considered. Typically, the viscosity between about 0.1-10.0 1/seconds shear rate is useful and enough data points are taken to fit to the well accepted power law model (see for instance: Chemical Engineering, by Coulson and Richardson, Pergamon, 1982 or Transport Phenomena, by Bird, Steward and Lightfoot, Wiley, 1960):

$$\mu = k(\gamma')^{(n-1)}$$

The value obtained for the log-log slope is (n−1) where n is the Shear Index and the value obtained for k is the Consistency Value in poise/(1/second).

Water Structurant

The non-lathering structured aqueous phase of the present invention comprises from about 0.1% to about 30%, preferably from about 0.5% to about 20%, more preferably from about 0.5% to about 10%, and even more preferably from about 0.5% to about 5%, by weight of the non-lathering structured aqueous phase, of a water structurant.

The water structurant is typically selected from the group consisting of inorganic water structurants, charged polymeric water structurants, water soluble polymeric structurants, associative water structurants, and mixtures thereof.

Non-limiting examples of inorganic water structurants for use in the personal cleansing composition include silicas, clays such as a synthetic silicates (Laponite XLG and Laponite XLS from Southern Clay), or mixtures thereof.

Non-limiting examples of charged polymeric water structurants for use in the personal cleansing composition include Acrylates/Vinyl Isodecanoate Crosspolymer (Stabylen 30 from 3V), Acrylates/C10-30 Alkyl Acrylate Crosspolymer (Pemulen TR1 and TR2), Carbomers, Ammonium Acryloyldimethyltaurate/VP Copolymer (Aristoflex AVC from Clariant), Ammonium Acryloyldimethyltaurate/Beheneth-25 Methacrylate Crosspolymer (Aristoflex HMB from Clariant), Acrylates/Ceteth-20 Itaconate Copolymer (Structure 3001 from National Starch), Polyacrylamide (Sepigel 305 from SEPPIC), or mixtures thereof.

Non-limiting examples of water soluble polymeric structurants for use in the personal cleansing composition include cellulosic gel, hydroxypropyl starch phosphate (Structure XL from National Starch), polyvinyl alcohol, or mixtures thereof.

Nonlimiting examples of associative water structurants for use in the personal cleansing composition include synthetic and natural gums and thickeners such as xanthan gum (Ketrol CG-T from CP Kelco), succinoglycan (Rheozan from Rhodia, gellum gum, pectin, alginates, starches including pregelatinized starches, modified starches, or mixtures thereof.

Water

The non-lathering structured aqueous phase of the present invention comprises from about 30% to about 99%, by weight of the non-lathering structured aqueous phase, of water. The non-lathering structured aqueous phase generally comprises more than about 50%, preferably more than about 60%, even more preferably more than about 70%, still more preferably more than about 80%, by weight of the non-lathering structured aqueous phase, of water.

The non-lathering structured aqueous phase will typically have a pH of from about 5 to about 8, more preferably from about 6 to about 7. The non-lathering structured aqueous phase can optionally comprise a pH regulator to facilitate the proper pH range. Preferably, the pH of the non-lathering structured aqueous phase will be within +/−0.25 pH units of the lathering aqueous phase.

Electrolyte

The non-lathering structured aqueous phase of the present invention can optionally further comprise electrolyte. Preferably, the electrolyte used in the non-lathering structured aqueous phase will be the same as the electrolyte used in the lathering phase, when present. Generally, the amount of electrolyte in the non-lathering structured aqueous phase is from about 0.1% by weight to about 15%, preferably from about 1% to about 6% by weight of the non-lathering structured aqueous phase, but may be varied if required. When both the non-lathering structured aqueous phase and the lathering cleansing phase comprise electrolyte, the level of electrolyte in the non-lathering structured aqueous phase is preferably at least about 30%, more preferably at least about 40%, even more preferably at least about 50%, and most preferably at least about 75% of the amount of electrolyte added to the lathering cleansing phase. Preferably, the level of electrolyte in the non-lathering structured aqueous phase will be less than about 150%, more preferably less than about 130%, and most preferably less than about 120% of the amount of electrolyte added to the lathering cleansing phase.

The non-lathering structured aqueous phase of the present compositions can further comprise optional ingredients such as those described hereinafter. Preferred optional ingredients for the non-lathering structured aqueous phase include pigments, pH regulators, and preservatives. In one embodiment, the non-lathering structured aqueous phase comprises a water structurant (e.g. acrylates/vinyl isodecanoate crosspolymer), water, a pH regulator (e.g. triethanolamine), and a preservative (e.g. 1,3-dimethylol-5,5-dimethylhydantoin ("DM-DMH" available from Lonza under the trade name GLY-DANT®)).

Lathering Cleansing Phase

The personal cleansing compositions of the present invention comprise a lathering cleansing phase that comprises a cleansing surfactant suitable for application to the skin or hair. Suitable surfactants for use herein include any known or otherwise effective cleansing surfactant which are suitable for application to the skin, and which are otherwise compatible with the other essential ingredients in the aqueous lathering cleansing phase of the compositions. These cleansing surfactants include anionic, nonionic, cationic, zwitterionic or amphoteric surfactants, or combinations thereof. Suitable surfactants are described in *McCutcheon's, Emulsifiers and Detergents*, 1989 *Annual*, published by M. C. Publishing Co., and in U.S. Pat. No. 3,929,678.

The lathering cleansing phase of the personal care compositions typically comprises a cleansing surfactant at concentrations ranging from about 1% to about 90%, more preferably from about 4% to about 50%, even more preferably from about 5% to about 30%, by weight of the lathering cleansing phase. The preferred pH range of the cleansing phase is from about 5 to about 8, more preferably about 6.

The lathering cleansing phase of the personal care compositions preferably produces a Total Lather Volume of at least about 500 ml, more preferably greater than about 600 ml, even more preferably greater than about 700 ml, even more preferably greater than about 800 ml, still more preferably greater than about 1000 ml, and still even more preferably greater than about 1250 ml as measured by the Lather Volume Test described hereinafter. The lathering cleansing phase of the personal care compositions preferably produces a Flash Lather Volume of at least about 200 ml, preferably greater than about 250 ml, even more preferably greater than about 300 ml, as measured by the Lather Volume Test described hereinafter.

Preferably, the lathering cleansing phase has a viscosity of greater than about 3,000 centipoise ("cps"), more preferably greater than about 10,000 cps, even more preferably greater than about 20,000 cps, and still more preferably greater than about 40,000 cps, as measured by the Viscosity Method described hereinafter.

Preferably, the lathering cleansing phase has a Yield Point of greater than about 0.1 Pascal (Pa), more preferably greater than about 1 Pascal, even more preferably greater than about 10 Pascal, and still more preferably greater than about 30 Pascal, as measured by the Yield Point Method described hereinafter.

Anionic surfactants suitable for use as cleansing surfactant in the lathering cleansing phase of the present compositions include alkyl and alkyl ether sulfates. These materials have the respective formula $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium, or triethanolamine. The alkyl ether sulfates are typically made as condensation products of ethylene oxide and mono-hydric alcohols having from about 8 to about 24 carbon atoms. Preferably, R has from about 10 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, preferably from about 3 to about 5, and more preferably with about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the lathering cleansing phase are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Other suitable anionic surfactants include water-soluble salts of the organic, sulfuric acid reaction products of the general formula $[R^1-SO_3-M]$, wherein $R^1$ is chosen from the group consisting of a straight or branched chain, saturated aliphatic hydrocarbon radical having from about 8 to about 24, preferably about 10 to about 18, carbon atoms; and M is a cation. Suitable examples are the salts of an organic sulfuric acid reaction product of a hydrocarbon of the methane series, including iso-, neo-, ineso-, and n-paraffins, having about 8 to about 24 carbon atoms, preferably about 10 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{10-18}$ n-paraffins.

Preferred anionic surfactants for use in the lathering cleansing phase include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, and combinations thereof.

Anionic surfactants with branched alkyl chains such as sodium trideceth sulfate, for example, are preferred in some embodiments. Mixtures of anionic surfactants can be used in some embodiments.

Other surfactants from the classes of amphoteric, zwitterionic surfactant, cationic surfactant, and/or nonionic surfactant can be incorporated in the lathering cleansing phase compositions.

Amphoteric surfactants suitable for use as cleansing surfactant in the lathering cleansing phase of the present compositions include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378.

Zwitterionic surfactants suitable for use as cleansing surfactant in the lathering cleansing phase include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Such suitable zwitterionic surfactants can be represented by the formula:

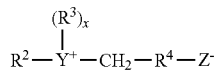

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Other zwitterionic surfactants suitable for use in the lathering cleansing phase include betaines, including high alkyl betaines such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gammacarboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in the present compositions.

Amphoacetates and diamphoacetates can also be used. Suitable amphoacetates have the formula:

and suitable diamphoacetate have the formula:

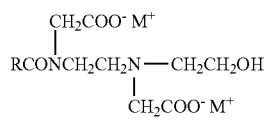

wherein R is an aliphatic group of 8 to 18 carbon atoms; and M is a cation such as sodium, potassium, ammonium, or substituted ammonium. Non-limiting examples of suitable amphoacetates and diamphoacetates include sodium lauroamphoacetate, sodium cocoamphoactetate, disodium lauroamphoacetate, and disodium cocodiamphoacetate.

Cationic surfactants can also be used in the lathering cleansing phase, but are generally less preferred, and preferably represent less than about 5%, by weight of the lathering cleansing phase.

Suitable nonionic surfactants for use in the lathering cleansing phase include condensation products of alkylene oxide groups (hydrophilic in nature) with an organic hydrophobic compound, which may be aliphatic or alkyl aromatic in nature.

Lamellar Structurant

The lathering cleansing phase of the present compositions optionally, but preferably, further comprise about 0.1% to 10% by wt. of a lamellar structurant which functions in the compositions to form a lamellar phase. It is believed the lamellar phase enhances the interfacial stability between the lathering cleansing phase and the non-lathering structured aqueous phase of the present compositions.

Suitable lamellar structurants include a fatty acid or ester derivatives thereof, a fatty alcohol, an ethoxylated fatty alcohol, trihydroxystearin (available from Rheox, Inc. under the trade name THIXCIN® R), or polymethyacrylamidopropyl trimonium chloride (available from Rhodia under the trade name POLYCARE® 133). If the lamellar structurant is a fatty acid, or an ester of fatty acid, the hydrocarbon backbone can be straight chained or branched. Preferably, the lamellar structurant is selected from lauric acid, fatty alcohols, ethoxylated fatty alcohols, or trihydroxystearin.

In a preferred embodiment of the present invention, the surfactant for use in the lathering cleansing phase exhibit Non-Newtonian shear thinning behavior (herein referred to as free flowing compositions) and can be mixtures of surfactants. Suitable surfactant mixtures can comprise water, at least one anionic surfactant, an electrolyte, and at least one alkanolamide. It has been found that by employing a lathering cleansing phase exhibiting Non-Newtonian shear thinning behavior, the stability of the resulting personal cleansing composition can be increased. The alkanolamide if present has the general structure of:

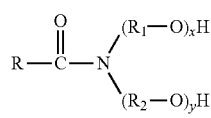

wherein R is $C_8$ to $C_{24}$, or preferably in some embodiments $C_8$ to $C_{22}$ or in other embodiments $C_8$ to $C_{18}$, saturated or unsaturated, straight chain or branched, aliphatic group; $R_1$ and $R_2$ are the same or different $C_2$-$C_4$ straight chain or branched aliphatic group; x is from 0 to 10; y is from 1 to 10; and wherein the sum of x and y is less than or equal to 10.

The amount of alkanolamide in the composition is typically about 0.1% to about 10%, by weight of the lathering cleansing phase, and in some embodiments is preferably from about 2% to about 5%, by weight of the lathering cleansing phase. Suitable alkanolamides include Cocamide MEA (Coco monethanolamide) and Cocamide MIPA (Coco monoisopropranolamide).

The electrolyte, if used, can be added per se to the composition or it can be formed in situ via the counter-ions included in one of the raw materials. The electrolyte preferably includes an anion comprising phosphate, chloride, sulfate or citrate and a cation comprising sodium, ammonium, potassium, magnesium or mixtures thereof. Some preferred electrolytes are sodium or ammonium chloride or sodium or ammonium sulfate. A preferred electrolyte is sodium chloride.

The electrolyte, when present, should be present in an amount, which facilitates formation of the free flowing composition. Generally, this amount is from about 0.1% by weight to about 15% by weight, preferably from about 1% to about 6% by weight of the lathering cleansing phase, but may be varied if required.

In one embodiment of the present invention, the lathering cleansing phase comprises an anionic surfactant (e.g. sodium trideceth sulfate), an amphoacetate surfactant (e.g. sodium lauroamphoacetate), and an alkanolamide (e.g. cocoamide MEA). The lathering cleansing phase of this embodiment preferably further comprises an electrolyte (e.g. sodium chloride).

Colorant

In a preferred embodiment the multi-phase personal cleansing composition comprises a colorant in at least one phase of the multi-phase personal cleansing composition. The composition comprises from about 0.00001% to about 10%, by weight of the composition of a colorant. Preferably, the multi-phase personal cleansing compositions comprises from about 0.0001% to about 1%, more preferably from about 0.001% to about 0.1%, even more preferably from about 0.005% to about 0.05%, by weight of the composition of a colorant.

The colorant, in a preferred embodiment, comprises metal ions. Preferably, the colorant is free of barium and aluminum ions which allows for improved lamellar phase stability. The colorant preferably maintains UV stability.

The colorants for use in the multi-phase personal cleansing compositions are selected from the group consisting of organic pigments, inorganic pigments, interference pigments, lakes, natural colorants, pearlescent agents, dyes, carmines, and mixtures thereof.

Non-limiting examples of colorants include: D&C Red 30 Talc Lake, D&C Red 7 Calcium Lake, D&C Red 34 Calcium Lake, Mica/Titanium Dioxide/Carmine Pigments (Clorisonne Red from Engelhard, Duocrome RB from Engelhard, Magenta from Rona, Dichrona RB from Rona), Red 30 Low Iron, D&C Red Lake Blend of Lake 27 & Lake 30, FD&C Yellow 5 Lake, Kowet Titanium Dioxide, Yellow Iron Oxide, D&C Red 30 Lake, D&C Red 28 Lake, Cos Red Oxide BC, Cos Iron Oxide Red BC, Cos Iron oxide Black BC, Cos Iron Oxide Yellow, Cos Iron Oxide Brown, Cos Iron Oxide Yellow BC, Euroxide Red Unsteril, Euroxide Black Unsteril, Euroxide Yellow Steril, Euroxide Black Steril, Euroxide Red, Euroxide Black, Hydrophobic Euroxide Black, Hydrophobic Euroxide Yellow, Hydrophobic Euroxide Red, D&C Yellow 6 Lake, D&C Yellow 5 Zr Lake, and mixtures of these colorants.

Optional Ingredients

A variety of suitable optional ingredients can be employed in the lathering cleansing phase and the non-lathering structured aqueous phase. Non-limiting optional ingredients include humectants and solutes. A variety of humectants and solutes can be employed and can be present at a level of from about 0.1% to about 50%, preferably from about 0.5% to about 35%, and more preferably from about 2% to about 20%, by weight of the personal care composition. Preferred humectants are glycerin and sorbitol.

Suitable optional ingredients further include skin conditioning agents. Nonionic polyethylene/polypropylene glycol polymers are preferably used as skin conditioning agents. Polymers useful herein that are especially preferred are PEG-2M wherein x equals 2 and n has an average value of about 2,000 (PEG 2-M is also known as Polyox WSR® N-10 from Union Carbide and as PEG-2,000); PEG-5M wherein x equals 2 and n has an average value of about 5,000 (PEG 5-M is also known as Polyox WSR® 35 and Polyox WSR® N-80, both from Union Carbide and as PEG-5,000 and Polyethylene Glycol 200,000); PEG-7M wherein x equals 2 and n has an average value of about 7,000 (PEG 7-M is also known as Polyox WSR® (N-750 from Union Carbide); PEG-9M wherein x equals 2 and n has an average value of about 9,000 (PEG 9-M is also known as Polyox WSR® N-3333 from Union Carbide); PEG-14 M wherein x equals 2 and n has an average value of about 14,000 (PEG 14-M is also known as Polyox WSR®-205 and Polyox WSR® N-3000 both from Union Carbide); and PEG-90M wherein x equals 2 and n has an average value of about 90,000 (PEG-90M is also known as Polyox WSR®-301 from Union Carbide.)

The multi-phase personal cleansing compositions of the present invention can additionally comprise an organic cationic deposition polymer in the lathering cleansing phase or the non-lathering structured aqueous phase as a deposition aid. Concentrations of the cationic deposition polymer preferably range from about 0.025% to about 3%, more preferably from about 0.05% to about 2%, even more preferably from about 0.1% to about 1%, by weight of the lathering cleansing phase composition.

Suitable cationic deposition polymers for use in the multi-phase personal cleansing composition of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal cleansing composition. The average molecular weight of the cationic deposition polymer is between about 5,000 to about 10 million, preferably at least about 100,000, more preferably at least about 200,000, but preferably not more than about 2 million, more preferably not more than about 1.5 million. The polymers also have a cationic charge density ranging from about 0.2 meq/gm to about 5 meq/gm, preferably at least about 0.4 meq/gm, more preferably at least about 0.6 meq/gm., at the pH of intended use of the personal cleansing composition, which pH will generally range from about pH 4 to about pH 9, preferably between about pH 5 and about pH 8.

Nonlimiting examples of cationic deposition polymers for use in the personal cleansing composition include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer KG, JR and LR series of polymers with the most preferred being KG-30M.

Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

Other suitable cationic deposition polymers include synthetic cationic polymers. The cationic polymers suitable for use in the cleansing composition herein are water soluble or dispersible, non crosslinked, cationic polymers having a cationic charge density of from about 4 meq/gm to about 7 meq/gm, preferably from about 4 meq/gm to about 6 meq/gm, more preferably from about 4.2 meq/gm to about 5.5 meq/gm. The select polymers also must have an average molecular weight of from about 1,000 to about 1 million, preferably from about 10,000 to about 500,000, more preferably from about 75,000 to about 250,000.

The concentration of the cationic polymer in the cleansing composition ranges about 0.025% to about 5%, preferably from about 0.1% to about 3%, more preferably from about 0.2% to about 1%, by weight of the composition.

A non-limiting example of a commercially available synthetic cationic polymer for use in the cleansing compositions is polymethyacrylamidopropyl trimonium chloride, available under the trade name Polycare 133, from Rhodia, Cranberry, N.J., U.S.A.

The cationic polymers herein are either soluble in the lathering cleansing phase, or preferably are soluble in a complex coacervate phase in the multi-phase personal cleansing composition formed by the cationic deposition polymer and the anionic surfactant component described hereinbefore. Complex coacervates of the cationic deposition polymer can also be formed with other charged materials in the personal cleansing composition.

Coacervate formation is dependent upon a variety of criteria such as molecular weight, component concentration, and ratio of interacting ionic components, ionic strength (including, modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", Cosmetics & Toiletries, Vol. 106, April 1991, pp 49-54, C. J. van Oss, "Coacervation, Complex-Coacervation and Flocculation", J. Dispersion Science and Technology, Vol. 9 (5,6), 1988-89, pp 561-573, and D. J. Burgess, "Practical Analysis of Complex Coacervate Systems", J. of Colloid anti Interface Science, Vol. 140, No. 1, November 1990, pp 227-238, which descriptions are incorporated herein by reference.

It is believed to be particularly advantageous for the cationic deposition polymer to be present in the personal cleansing composition in a coacervate phase, or to form a coacervate phase upon application or rinsing of the cleansing composition to or from the skin. Complex coacervates are believed to more readily deposit on the skin, which results in improved deposition of the benefit materials. Thus, in general, it is preferred that the cationic deposition polymer exists in the personal cleansing composition as a coacervate phase or forms a coacervate phase upon dilution. If not already a coacervate in the personal cleansing composition, the cationic deposition polymer will preferably exist in a complex coacervate form in the cleansing composition upon dilution with water.

Techniques for analysis of formation of complex coacervates are known in the art. For example, centrifugation analyses of the personal cleansing compositions, at any chosen stage of dilution, can be utilized to identify whether a coacervate phase has formed.

Other non-limiting examples of these optional ingredients include vitamins and derivatives thereof (e.g., ascorbic acid, vitamin E, tocopheryl acetate, and the like); sunscreens; thickening agents (e.g., polyol alkoxy ester, available as Crothix from Croda); preservatives for maintaining the antimicrobial integrity of the cleansing compositions (e.g., DMDMH); anti-acne medicaments (resorcinol, salicylic acid, and the like); antioxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), and the like (e.g., clove oil, menthol, camphor, eucalyptus oil, and eugenol). These materials can be used at ranges sufficient to provide the required benefit, as would be obvious to one skilled in the art.

To the extent any optional ingredients described herein include specific materials described hereinbefore as water structurants or lamellar structurants, such materials shall be considered water structurants or lamellar structurants for the purposes of the present invention.

Test Methods

Lather Volume Test

Lather volume of a multi-phase personal cleansing composition, or of a non-lathering structured aqueous phase or lathering cleaning phase of a personal cleansing composition, is measured using a graduated cylinder and a tumbling apparatus. A 1,000 ml graduated cylinder is used which is marked in 10 ml increments and has a height of 14.5 inches at the 1,000 ml mark from the inside of its base (for example, Pyrex No. 2982). Distilled water (100 grams at 23° C.) is added to the graduated cylinder. The cylinder is clamped in a rotating device, which clamps the cylinder with an axis of rotation that transects the center of the graduated cylinder. One gram of the total personal cleansing composition (0.5 g of the lathering cleansing phase and 0.5 g of the non-lathering structured aqueous phase when measuring the total product, or 1 g of the lathering cleansing phase or non-lathering structured aqueous phase when the measuring the lathering cleansing phase or non-lathering structured aqueous phase only) is added into the graduated cylinder and the cylinder is capped. The cylinder is rotated at a rate of 10 revolutions in about 20 seconds, and stopped in a vertical position to complete the first rotation sequence. A timer is set to allow 30 seconds for the lather thus generated to drain. After 30 seconds of such drainage, the first lather volume is measured to the nearest 10 ml mark by recording the lather height in ml up from the base (including any water that has drained to the bottom on top of which the lather is floating).

If the top surface of the lather is uneven, the lowest height at which it is possible to see halfway across the graduated cylinder is the first lather volume (ml). If the lather is so coarse that a single or only a few foam cells ("bubbles") reach across the entire cylinder, the height at which at least 10 foam cells are required to fill the space is the first lather volume, also in ml up from the base. Foam cells larger than one inch in any dimension, no matter where they occur, are designated as unfilled air instead of lather. Foam that collects on the top of the graduated cylinder but does not drain is also incorporated in the measurement if the foam on the top is in its own continuous layer, by adding the ml of foam collected there using a ruler to measure thickness of the layer, to the ml of foam measured up from the base. The maximum foam height is 1,000 ml (even if the total foam height exceeds the 1,000 ml mark on the graduated cylinder). One minute after the first rotation is completed, a second rotation sequence is commenced which is identical in speed and duration to the first rotation sequence. The second lather volume is recorded in the same manner as the first, after the same 30 seconds of drainage time. A third sequence is completed and the third lather volume is measured in the same manner, with the same pause between each for drainage and taking the measurement.

The lather result after each sequence is added together and the Total Lather Volume determined as the sum of the three measurements, in ml. The Flash Lather Volume is the result after the first rotation sequence only, in ml, i.e., the first lather volume. Compositions according to the present invention perform significantly better in this test than similar compositions in conventional emulsion form.

Viscosity Method

The Wells-Brookfield Cone/Plate Model DV-II+ Viscometer can be used to determine the viscosity of the non-lathering structured aqueous phase and the lathering cleansing phase herein. The determination is performed at 25° C. with the 2.4 cm 2° cone measuring system with a gap of 0.013 mm between the two small pins on the respective cone and plate. The measurement is performed by injecting 0.5 ml of the sample, and then, rotating the cone at a set speed of 1 rpm. The resistance to the rotation of the cone produces a torque that is proportional to the shear stress of the liquid sample. The amount of torque is read at 2 mins after loading the sample and computed by the viscometer into absolute centipoise units (mPa*s) based on the geometric constant of the cone, the rate of rotation, and the stress related torque.

Yield Point Method

A TA Instruments AR2000 Controlled Stress Rheometer can be used to determine the Yield Point of the non-lathering structured aqueous phase or the lathering cleansing phase. For purpose herein, the Yield Point is the amount of stress required to produce a strain of 1% on the liquid non-lathering structured aqueous phase or the lathering cleansing phase. The determination is performed at 25° C. with the 4 cm diameter parallel plate measuring system and a 1 mm gap. The determination is performed via the programmed application of a shear stress (typically from about 0.1 Pa to about 500 Pa 0) over a time interval of 5 minutes. It is this amount of stress that results in a deformation of the sample, a shear stress vs. strain curve can be created. From this curve, the Yield Point of the liquid non-lathering structured aqueous phase can be determined. The liquid non-lathering structured aqueous phase or the lathering cleansing phase are measured either prior to combining in the composition, or after combining in the composition by separating the compositions by suitable physical separation means, such as centrifugation, pipetting, cutting away mechanically, rinsing, filtering, or other separation means.

Water Mobility Method

The water mobility of non-lathering structured aqueous phase is determined by Pulsed-NMR method. A Maran Ultra Low Field Pulsed NMR, 23 MHz, CPMG pulse sequence, with thermal control regulated at 24-29° C. is used for measuring water mobility. The non-lathering structured aqueous phase sample is first placed in the Pulsed-NMR test tube and then exposed to excitation of a pulsed ratio frequency (23 MHz). The acquisition and data processing parameters are listed in the table below.

| ACQUISITION PARAMETERS | |
| --- | --- |
| 90 Degree pulse | 6.9 μs |
| 180 Degree pulse | 13.5 μs |
| Probe dead time | 4.0 μs |
| Receiver dead time | 3.0 μs |
| Spectrometer frequency | 23.10 MHz |
| Offset from SF | −25116.83 Hz |
| Filter width | 1,000,000 Hz |
| Dwell time | 1 μs |
| Points per echo | 1 |
| Number of echoes | 8192 |
| Number of scans | 8 |

| ACQUISITION | |
| --- | --- |
| Receiver gain | 0.50% |
| Relaxation delay | 10,000,000 μs |
| 90-180 Degree pulse gap | 100.0 μs |
| 90 Degree pulse phase list | 0213 |
| Receiver phase list | 0213 |
| 180 Degree pulse phase list | 1122 |
| Dummy scans | 2 |
| PROCESSING PARAMETERS | |
| Line broadening | 0.00 |
| Number of smoothing points | 0 |
| Detector phase | 2.81 |
| Zero order phase correction | 0.00 |
| First order phase correction | 0.00 |
| Pivot point for first order phase correction | 0 |
| Peak picker relative threshold | 4.0% |
| Peak picker Rayleigh factor | 50% |
| Peak picker P-factor | 0 |
| RESULTS | Report area % and T2 time of the largest water containing peak. |

The relaxation decay constant (T2 time) is calculated by measuring the signal decay profile. The T2 time (in seconds) of the largest water containing peak is reported as Water Mobility. A high T2 relaxation time indicates high water mobility. A low T2 relaxation time indicates low water mobility (i.e., a more structured system).

Correlated Haze Index Method

The Macbeth Color Measurement Sytem-Gretag Macbeth Model 7000 with sphere geometry optical head is used to perform the Correlated Haze Index Method. The instrument needs to be calibrated on both reflectance and transmission modes. Both of these calibrations are used to obtain the Correlated Haze Index.

To prepare the sample, the composition is centrifuged at 3000 rpm for about 3 minutes to remove any air bubbles that may be present. Then, slowly pour the composition into an optical cell to avoid air entrapment. If the air entrapment occurs, allow the sample to sit for 30 minutes at room temperature to de-aerate. If air bubbles persist, first empty the cell, then clean and dry the cell and then refill as before. Remove any composition spilled on the outside surface of the cell by for example wiping. The sample of the composition must be within 2° C. of the original calibration temperature.

Once the sample is prepared, the instrument should be on traditional Lab setting, using C Illuminate, 2 degree observer angle and no averaging. Next configure the instrument setting to CRIOLL setting. This is done by changing the specular component to included, the UV to excluded, and the measurement mode to reflectance. These changes are made without any sample cell holder inside the instrument. Next, place a large sample cell holder without sample inside the instrument and calibrate the instrument according to on screen prompts. Switch the measurement mode to transmission, then the instrument will show BTIOLL setting. Calibrate the instruments by following onscreen prompts.

Next, switch the instrument to measurement mode, Correlated Haze. The instrument setting will now be XHIOLL. Calibrate the instrument by following the onscreen prompts. The new instrument setting will be CHIOLL. The operator then clicks the indices icon on the toolbar to bring up the display that shows Correlated Haze results. Run an empty cell as the standard.

Fill the optical cell with the sample of the composition to be analyzed, making sure there is no air entrapment. Run as a trial and report percent Correlated Haze results. The calibration of the instrument must be performed at least every 8 hours.

Method of Use

The multi-phase personal cleansing compositions of the present invention are preferably applied topically to the desired area of the skin or hair in an amount sufficient to provide effective delivery of the skin cleansing agent and skin benefit agents to the applied surface. The compositions can be applied directly to the skin or indirectly via the use of a cleansing puff, washcloth, sponge or other implement. The compositions are preferably diluted with water prior to, during, or after topical application, and then subsequently rinsed or wiped off of the applied surface, preferably rinsed off of the applied surface using water or a water-insoluble substrate in combination with water.

The present invention is therefore also directed to methods of cleansing the skin through the above-described application of the compositions of the present invention. The methods of the present invention are also directed to a method of providing effective delivery of the desired skin active agent, and the resulting benefits from such effective delivery as described herein, to the applied surface through the above-described application of the compositions of the present invention.

Method of Manufacture

The multi-phase personal cleansing compositions of the present invention may be prepared by any known or otherwise effective technique, suitable for making and formulating the desired multi-phase product form. It is effective to combine toothpaste-tube filling technology with a spinning stage design. Additionally, the present invention can be prepared by the method and apparatus as disclosed in U.S. Pat. No. 6,213,166. The method and apparatus allows two or more compositions to be filled with a spiral configuration into a single container. The method requires that at least two nozzles be employed to fill the container. The container is placed on a static mixer and spun as the composition is introduced into the container.

Alternatively, it is effective to combine at least two phases by first placing the separate compositions in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The pattern is selected from the group consisting of striped, marbled, geometric, and mixtures thereof. The next step involves pumping the product that was mixed in the blending section via a hose into a single nozzle, then placing the nozzle into a container and filing the container with the resulting product. Specific non-limiting examples of such methods as they are applied to specific embodiments of the present invention are described in the following examples.

If the personal cleansing compositions contain stripes of varying colors it can be desirable to package these compositions in a transparent or translucent package such that the consumer can view the pattern through the package. Because of the viscosity of the subject compositions it may also be desirable to include instructions to the consumer to store the package upside down, on its cap to facilitate dispensing.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All parts, ratios, and percentages herein, in the Specification, Examples, and claims, are by weight and all numerical limits are used with the normal degree of accuracy afforded by the art, unless otherwise specified.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Each of the examples below are of personal care compositions comprising 50%, by weight of the personal care composition, of a lathering cleansing phase and 50%, by weight of the personal care composition, of a non-lathering structured aqueous phase. The amount of each component in a particular phase is provided as a weight percent based on the weight of the particular phase that contains the component.

Examples 1-3

The following examples described in Table 1 are non-limiting examples of lathering cleansing phase and non-lathering structured aqueous phase compositions.

TABLE 1

Lathering Cleansing Phase and Non-Lathering Structured Aqueous Phase Compositions

| Ingredient | Example 1 wt % | Example 2 wt % | Example 3 wt % |
| --- | --- | --- | --- |
| I. Lathering Cleansing Phase Composition | | | |
| Ammonium Laureth-3 Sulfate | 3.0 | 3.0 | 3.0 |
| Sodium Lauroamphoacetate (Miranol L-32 Ultra from Rhodia) | 16.7 | 16.7 | 16.7 |
| Ammonium Lauryl Sulfate | 1.0 | 1.0 | 1.0 |
| Lauric Acid | 0.9 | 0.9 | 0.9 |
| Trihydroxystearin (Thixcin R) | 2.0 | 2.0 | 2.0 |
| Guar Hydroxypropyltrimonium Chloride (N-Hance 3196 from Aqualon) | 0.17 | 0.75 | 0.75 |
| Guar Hydroxypropyltrimonium Chloride (Jaguar C-17 from Rhodia) | 0.58 | — | — |
| Polyquaterium 10 (UCARE polymer JR-30M from Amerchol) | 0.45 | — | — |
| Polymethacrylamidopropyltrimonium Chloride (Polycare 133 from Rhodia) | — | 0.24 | — |
| Polyquaternium-39 (Merqurt Plus 3300 from Calgon) | — | 0.81 | — |
| PEG 90M (Polyox WSR 301 from Union Carbide) | 0.25 | — | — |
| PEG-14M (Polyox WSR N-3000 H from Union Carbide) | 0.45 | 2.45 | 2.45 |
| Linoleamidoprypyl PG-Dimonium Chloride Phosphate Dimethicone (Monasil PLN from Uniqema) | — | 1.0 | 4.0 |
| Glycerin | 1.4 | 4.9 | 4.9 |
| Sodium Chloride | 0.3 | 0.3 | 0.3 |
| Sodium Benzoate | 0.25 | 0.25 | 0.25 |
| Disodium EDTA | 0.13 | 0.13 | 0.13 |
| Glydant | 0.37 | 0.37 | 0.37 |

TABLE 1-continued

Lathering Cleansing Phase and Non-Lathering Structured Aqueous Phase Compositions

| Ingredient | Example 1 wt % | Example 2 wt % | Example 3 wt % |
|---|---|---|---|
| Citric Acid | 1.6 | 0.95 | 0.95 |
| Titanium Dioxide | 0.5 | 0.5 | 0.5 |
| Perfume | 0.5 | 0.5 | 0.5 |
| Water | Q.S. | Q.S. | Q.S. |
| (pH) | (6.0) | (6.0) | (6.0) |
| II. Non-Lathering Structured Aqueous Phase Composition | | | |
| Acrylates/Vinyl Isodecanoate Crosspolymer (Stayblen 30 from 3V) | 0.8 | 1.0 | 1.2 |
| Triethanolamine | 0.8 | 1.0 | 1.2 |
| Glydant | 0.37 | 0.37 | 0.37 |
| Red 30 Talc Lake (From Sun Chemical) | 0.01 | 0.01 | 0.01 |
| Water and Minors | Q.S. | Q.S. | Q.S. |
| (pH) | (7.0) | (7.0) | (7.0) |

The compositions described above can be prepared by conventional formulation and mixing techniques. Prepare cleansing composition 1 by first creating the following premixes: citric acid in water premix at 1:3 ratio, Guar polymer premix with Jaguar C-17 and N-Hance 3196 in water at 1:10 ratio, UCARE premix with JR-30M in water at about 1:30 ratio, and Polyox premix with PEG-90M and PEG-14M in Glycerin at about 1:2 ratio. Then, add the following ingredients into the main mixing vessel: ammonium lauryl sulfate, ammonium laureth-3 sulfate, citric acid premix, Miranol L-32 ultra, sodium chloride, sodium benzoate, disodium EDTA, lauric acid, Thixcin R, Guar premix, UCARE premix, Polyox Premix, and the rest of water. Heat the vessel with agitation until it reaches 190° F. (88° C.). Let it mix for about 10 min. Cool the batch with a cold water bath with slow agitation until it reaches 110° F. (43° C.). Add the following ingredients: Glydant, perfume, Titanium Dioxide. Keep mixing until a homogeneous solution forms.

The cleansing composition 2 can be prepared by first creating the following premixes: citric acid in water premix at 1:3 ratio, Guar polymer premix with N-Hance 3196 in water at 1:10 ratio, and Polyox premix with PEG-14M in Glycerin at about 1:2 ratio. Then, add the following ingredients into the main mixing vessel: ammonium lauryl sulfate, ammonium laureth-3 sulfate, citric acid premix, Miranol L-32 ultra, sodium chloride, sodium benzoate, disodium EDTA, lauric acid, Thixcin R, Guar premix, Polyox Premix, Polycare 133, Merquat Plus 3300, Monasil PLN, and the rest of water. Heat the vessel with agitation until it reaches 190° F. (88° C.). Let it mix for about 10 min. Cool the batch with a cold water bath with slow agitation until it reaches 110° F. (43° C.). Add the following ingredients: Glydant, perfume, Titanium Dioxide. Keep mixing until a homogeneous solution forms.

The cleansing composition 3 can be prepared by first creating the following premixes: citric acid in water premix at 1:3 ratio, Guar polymer premix with N-Hance 3196 in water at 1:10 ratio, and Polyox premix with PEG-14M in Glycerin at about 1:2 ratio. Then, add the following ingredients into the main mixing vessel: ammonium lauryl sulfate, ammonium laureth-3 sulfate, citric acid premix, Miranol L-32 ultra, sodium chloride, sodium benzoate, disodium EDTA, lauric acid, Thixcin R, Guar premix, Polyox Premix, Monasil PLN, and the rest of water. Heat the vessel with agitation until it reaches 190° F. (88° C.). Let it mix for about 10 min. Cool the batch with a cold water bath with slow agitation until it reaches 110° F. (43° C.). Add the following ingredients: Glydant, perfume, Titanium Dioxide. Keep mixing until a homogeneous solution forms.

The non-lathering structured aqueous phase can be prepared by slowly adding Stabylen 30 into water in a mixing vessel. Then, add Triethanolamine, Glydant, cosmetic pigment with agitation. Mix until homogeneous.

The lathering cleansing and non-lathering structured aqueous phases can be combined by first placing the separate phases in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The pattern is selected from the group consisting of striped, marbled, geometric, and mixtures thereof. The next step involves pumping the product that was mixed in the blending section via a hose into a single nozzle, then placing the nozzle into a container and filing the container with the resulting product. The stripe size is about 6 mm in width and 100 mm in length. The products remain stable at ambient for at least 180 days.

Examples 4-6

The following examples described in Table 2 are non-limiting examples of lathering cleansing phase and non-lathering structured aqueous phase compositions of the present invention.

TABLE 2

Lathering Cleansing Phase and Non-Lathering Structured Aqueous Phase Compositions

| Ingredient | Example 4 wt % | Example 5 wt % | Example 6 wt % |
|---|---|---|---|
| I. Lathering Cleansing Phase Composition | | | |
| Miracare SLB-365 (from Rhodia) (Sodium Trideceth Sulfate, Sodium Lauramphoacetate, Cocamide MEA) | 47.4 | 47.4 | 47.4 |
| Cocamide MEA | 3.0 | 3.0 | 3.0 |
| Guar Hydroxypropyltrimonium Chloride (N-Hance 3196 from Aqualon) | 0.7 | 0.7 | 0.7 |
| PEG 90M (Polyox WSR 301 from Dow Chemical) | 0.2 | 0.2 | 0.2 |
| Glycerin | 0.8 | 0.8 | 0.8 |
| Sodium Chloride | 3.5 | 3.5 | 3.5 |
| Disodium EDTA | 0.05 | 0.05 | 0.05 |
| Glydant | 0.67 | 0.67 | 0.67 |
| Citric Acid | 0.4 | 0.4 | 0.4 |
| Perfume | 2.0 | 2.0 | 2.0 |
| Red 30 Talc Lake (From Sun Chemical) | 0.01 | 0.01 | 0.01 |
| Water | Q.S. | Q.S. | Q.S. |
| (pH) | (6.0) | (6.0) | (6.0) |
| II. Non-Lathering Structured Aqueous Phase Composition | | | |
| Acrylates/Vinyl Isodecanoate Crosspolymer (Stayblen 30 from 3V) | 1.0 | — | — |
| Carbomer Ultrez 21 | — | 1.0 | — |
| Ammonium Acryloyldimethyltaurate/Beheneth-25 Methacrylate Crosspolymer (Aristoflex HMB from Clariant) | — | — | 1.0 |
| Triethanolamine | 1.0 | 1.0 | 1.0 |
| Glydant | 0.37 | 0.37 | 0.37 |
| Water and Minors | Q.S. | Q.S. | Q.S. |
| (pH) | (7.0) | (7.0) | (7.0) |

The compositions described above can be prepared by conventional formulation and mixing techniques. The lathering cleansing phase composition can be prepared by forming the following premixes: adding citric acid into water at 1:1 ratio to form a citric acid premix, add polyox WSR-301 into glycerin at 1:3 ratio to form a polyox-glycerin premix, and add cosmetic pigment into glycerin at 1:20 ratio to form a pigment-glycerin premix and mix well using a high shear mixer. Then add the following ingredient in the main mixing vessel in the following sequence: water, N-Hance 3196, polyox premix, citric acid premix, disodium EDTA, and Miracare SLB-365. After mixing for 30 mins, begin heating the batch to 120 F. Add CMEA and mix until homogeneous. Then cool the batch to ambient temperature and add the following ingredients: sodium chloride, glydant, cosmetic pigment premix and perfume. Mix the batch for 60 mins. Check pH and adjust pH using citric acid or caustic solution if needed.

The non-lathering structured aqueous phase can be prepared by slowly adding Structurant (Stabylen 30, Carbomer Ultrez 21, Aristoflex HMB) into water in a mixing vessel. Then, add Triethanolamine, and Glydant with agitation. Mix until homogeneous.

The cleansing and non-lathering structured aqueous phases can be combined by first placing the separate phases in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The pattern is selected from the group consisting of striped, marbled, geometric, and mixtures thereof. The next step involves pumping the product that was mixed in the blending section via a hose into a single nozzle, then placing the nozzle into a container and filing the container with the resulting product. The stripe size is about 6 mm in width and 100 mm in length. The products remain stable at ambient for at least 180 days.

Examples 7-9

The following examples described in Table 3 are non-limiting examples of lathering cleansing phase and non-lathering structured aqueous phase compositions of the present invention.

TABLE 3

Lathering Cleansing Phase and Non-Lathering Structured Aqueous Phase Compositions

| Ingredient | Example 7 wt % | Example 8 wt % | Example 9 wt % |
| --- | --- | --- | --- |
| I. Lathering Cleansing Phase Composition | | | |
| Miracare SLB-365 (from Rhodia) (Sodium Trideceth Sulfate, Sodium Lauramphoacetate, Cocamide MEA) | 47.4 | 47.4 | 47.4 |
| Cocamide MEA | 3.0 | 3.0 | 3.0 |
| Guar Hydroxypropyltrimonium Chloride (N-Hance 3196 from Aqualon) | 0.7 | 0.7 | 0.7 |
| PEG 90M (Polyox WSR 301 from Dow Chemical) | 0.2 | 0.2 | 0.2 |
| Sodium Chloride | 3.5 | 3.5 | 3.5 |
| Disodium EDTA | 0.05 | 0.05 | 0.05 |
| Glydant | 0.67 | 0.67 | 0.67 |
| Citric Acid | 0.4 | 0.4 | 0.4 |
| Perfume | 2.0 | 2.0 | 2.0 |
| Water | Q.S. | Q.S. | Q.S. |
| (pH) | (6.0) | (6.0) | (6.0) |
| II. Non-Lathering Structured Aqueous Phase Composition | | | |
| Xanthan Gum (Keltrol from CP Kelco) | 1.0 | — | — |
| Succinoglycan (Rheozan from Rhodia) | — | 1.0 | — |
| Structure XL (from National Starch) | — | — | 6.0 |
| Glydant | 0.37 | 0.37 | 0.37 |
| Red 30 Talc Lake (From Sun Chemical) | 0.01 | 0.01 | 0.01 |
| Water and Minors | Q.S. | Q.S. | Q.S. |
| (pH) | (7.0) | (7.0) | (7.0) |

The compositions described above can be prepared by conventional formulation and mixing techniques. The lathering cleansing phase composition can be prepared by first adding citric acid into water at 1:3 ratio to form a citric acid premix. Then add the following ingredients into the main mixing vessel in the following sequence: water, Miracare SLB-365, sodium chloride, sodium benzoate, Disodium EDTA, glydant. Start agitation of the main mixing vessel. In a separate mixing vessel, disperse polymers (N-Hance 3196) in water at 1:10 ratio and form a polymer premix. Add the completely dispersed polymer premix into the main mixing vessel with continuous agitation. Disperse Polyox WSR 301 in water and then add to the main mixing vessel. Heat the batch to 120 F. Then, add cocamide MEA and mix until homogeneous. Then, cool the batch to ambient temperature and add the rest of the water and perfume into the batch. Keep agitation until a homogenous.

The non-lathering structured aqueous phase can be prepared by slowly adding aqueous Structurant (Keltrol CG-T, Rheozan, and Structure XL) into water in a mixing vessel. Then, add Glydant, cosmetic pigment with agitation. Mix until homogeneous.

The lathering cleansing and non-lathering structured aqueous phases can be combined by first placing the separate phases in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The pattern is selected from the group consisting of striped, marbled, geometric, and mixtures thereof. The next step involves pumping the product that was mixed in the blending section via a hose into a single nozzle, then placing the nozzle into a container and filing the container with the resulting product. The stripe size is about 6 mm in width and 100 mm in length. The products remain stable at ambient for at least 180 days.

Examples 10-12

The following examples described in Table 4 are non-limiting examples of lathering cleansing phase and non-lathering structured aqueous phase compositions of the present invention.

TABLE 4

Lathering Cleansing Phase and Non-Lathering Structured Aqueous Phase Compositions

| Ingredient | Example 10 wt % | Example 11 wt % | Example 12 wt % |
|---|---|---|---|
| I. Lathering Cleansing Phase Composition | | | |
| Miracare SLB-365 (from Rhodia) (Sodium Trideceth Sulfate, Sodium Lauramphoacetate, Cocamide MEA) | 47.4 | 47.4 | 47.4 |
| Cocamide MEA | 3.0 | 3.0 | 3.0 |
| Guar Hydroxypropyltrimonium Chloride (N-Hance 3196 from Aqualon) | 0.7 | 0.7 | 0.7 |
| PEG 90M (Polyox WSR 301 from Dow Chemical) | 0.2 | 0.2 | 0.2 |
| Glycerin | 0.8 | 0.8 | 0.8 |
| Sodium Chloride | 3.5 | 3.5 | 3.5 |
| Disodium EDTA | 0.05 | 0.05 | 0.05 |
| Glydant | 0.67 | 0.67 | 0.67 |
| Citric Acid | 0.4 | 0.4 | 0.4 |
| Perfume | 2.0 | 2.0 | 2.0 |
| Red 7 Ca Lake (From LCW) | 0.01 | 0.01 | 0.01 |
| Water | Q.S. | Q.S. | Q.S. |
| (pH) | (6.0) | (6.0) | (6.0) |
| II. Non-Lathering Structured Aqueous Phase Composition | | | |
| Acrylates/Vinyl Isodecanoate Crosspolymer (Stabylen 30 from 3V) | 1.0 | 1.0 | 1.0 |
| Xanthan gum (Keltrol CGT from CP Kelco) | 1.0 | — | — |
| succinoglycan (Rheozan from Rhodia) | — | 1.0 | — |
| Structure XL (from National Starch) | — | — | 6.0 |
| Triethanolamine | 1.5 | 1.5 | 1.5 |
| Sodium Chloride | 3.5 | 3.5 | 3.5 |
| Glydant | 0.37 | 0.37 | 0.37 |
| Water and Minors | Q.S. | Q.S. | Q.S. |
| (pH) | (6.0) | (6.0) | (6.0) |

The compositions described above can be prepared by conventional formulation and mixing techniques. The lathering cleansing phase composition can be prepared by forming the following premixes: adding citric acid into water at 1:1 ratio to form a citric acid premix, add polyox WSR-301 into glycerin at 1:3 ratio to form a polyox-glycerin premix, and add cosmetic pigment into glycerin at 1:20 ratio to form a pigment-glycerin premix and mix well using a high shear mixer. Then, add the following ingredient in the main mixing vessel in the following sequence: water, N-Hance 3196, polyox premix, citric acid premix, disodium EDTA, and Miracare SLB-365. Mix for 30 mins, then begin heating the batch to 120 F. Add CMEA and mix until homogeneous. Then, cool the batch to ambient temperature and add the following ingredients: sodium chloride, glydant, cosmetic pigment premix and perfume. Mix the batch for 60 mins. Check pH and adjust pH using citric acid or caustic solution if needed.

The non-lathering structured aqueous phase can be prepared by slowly adding Stabylene 30 into water with continuous mixing. Then, add other water structurant (Keltrol CG-T, Rheozan, and Structure XL) into the mixing vessel. Then, add Triethanolamine. The batch becomes viscous. Add sodium chloride, glydant and mix until homogeneous.

The lathering cleansing and non-lathering structured aqueous phases can be combined by first placing the separate phases in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The pattern is selected from the group consisting of striped, marbled, geometric, and mixtures thereof. The next step involves pumping the product that was mixed in the blending section via a hose into a single nozzle, then placing the nozzle into a container and filing the container with the resulting product. The stripe size is about 6 mm in width and 100 mm in length. The products remain stable at ambient for at least 180 days.

Examples 13-15

The following examples described in Table 5 are non-limiting examples of lathering cleansing phase and non-lathering structured aqueous phase compositions of the present invention.

TABLE 5

Lathering Cleansing Phase and Non-Lathering Structured Aqueous Phase Compositions

| Ingredient | Example 13 wt % | Example 14 wt % | Example 15 wt % |
|---|---|---|---|
| I. Lathering Cleansing Phase Composition | | | |
| Miracare SLB-365 (from Rhodia) (Sodium Trideceth Sulfate, Sodium Lauramphoacetate, Cocamide MEA) | 37.9 | 37.9 | 37.9 |
| Cocamide monoethanolamine | 2.4 | 2.4 | 2.4 |
| Guar Hydroxypropyltrimonium Chloride (N-Hance 3196 from Aqualon) | 0.56 | 0.56 | 0.56 |
| PEG 90M (Polyox WSR 301 from Dow Chemical) | 0.16 | 0.16 | 0.16 |
| Glycerin | 0.64 | 0.64 | 0.64 |
| Sodium Chloride | 2.8 | 2.8 | 2.8 |
| Disodium EDTA | 0.04 | 0.04 | 0.04 |
| Glydant | 0.54 | 0.54 | 0.54 |
| Citric Acid | 0.32 | 0.32 | 0.32 |
| Perfume | 2.0 | 2.0 | 2.0 |
| Red 7 Ca Lake (From LCW) | 0.01 | 0.01 | 0.01 |
| Superwhite Protopet Petrolatum (from WITCO) | 16 | 16 | 16 |
| Hydrobrite 1000 White Mineral Oil (from WITCO) | 4 | 4 | 4 |
| Water | Q.S. | Q.S. | Q.S. |
| (pH) | (6.0) | (6.0) | (6.0) |
| II. Non-Lathering Structured Aqueous Phase Composition | | | |
| Acrylates/Vinyl Isodecanoate Crosspolymer (Stayblen 30 from 3V) | 1.0 | 1.0 | 1.0 |
| Xanthan gum (Keltrol CGT from CP Kelco) | 1.0 | — | — |
| Succinoglycan (Rheozan from Rhodia) | — | 1.0 | — |

TABLE 5-continued

Lathering Cleansing Phase and Non-Lathering Structured Aqueous Phase Compositions

| Ingredient | Example 13 wt % | Example 14 wt % | Example 15 wt % |
|---|---|---|---|
| Structure XL (from National Starch) | — | — | 6.0 |
| Triethanolamine | 1.5 | 1.5 | 1.5 |
| Sodium Chloride | 3.5 | 3.5 | 3.5 |
| Glydant | 0.37 | 0.37 | 0.37 |
| Water and Minors | Q.S. | Q.S. | Q.S. |
| (pH) | (6.0) | (6.0) | (6.0) |

The compositions described above can be prepared by conventional formulation and mixing techniques. The lathering cleansing phase composition can be prepared by forming the following premixes: adding citric acid into water at 1:1 ratio to form a citric acid premix, add polyox WSR-301 into glycerin at 1:3 ratio to form a polyox-glycerin premix, and add cosmetic pigment into glycerin at 1:20 ratio to form a pigment-glycerin premix and mix well using a high shear mixer. Then add the following ingredient in the main mixing vessel in the following sequence: water, N-Hance 3196, polyox premix, citric acid premix, disodium EDTA, and Miracare SLB-365. After mixing for 30 mins, begin heating the batch to 120 F. Add CMEA and mix until homogeneous. Then cool the batch to ambient temperature and add the following ingredients: sodium chloride, glydant, cosmetic pigment premix, and perfume. Mix the batch for 60 mins. Check pH and adjust pH using citric acid or caustic solution if needed. In a separate vessel, add superwhite protopet petrolatum and hydrobrite 1000 white mineral oil. Heat the vessel to 190 F. Then, combine the lipid blend and the surfactant mixture through a static mixer (12 element Koch mixer) to form the final lathering phase.

The non-lathering structured aqueous phase can be prepared by slowly adding Stabylene 30 into water with continuous mixing. Then add other water structurant (Keltrol CG-T, Rheozan, and Structure XL) into the mixing vessel. Then add Triethanolamine. The batch becomes viscous. Add sodium chloride, glydant and mix until homogeneous.

The lathering cleansing and non-lathering structured aqueous phases can be combined by first placing the separate phases in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The pattern is selected from the group consisting of striped, marbled, geometric, and mixtures thereof. The next step involves pumping the product that was mixed in the blending section via a hose into a single nozzle, then placing the nozzle into a container and filing the container with the resulting product. The stripe size is about 6 mm in width and 100 mm in length. The products remain stable at ambient for at least 180 days.

Examples 16-18

The following examples described in Table 6 are non-limiting examples of lathering cleansing phase and non-lathering structured aqueous phase compositions of the present invention.

TABLE 6

Lathering Cleansing Phase and Non-Lathering Structured Aqueous Phase Compositions

| Ingredient | Example 16 wt % | Example 17 wt % | Example 18 wt % |
|---|---|---|---|
| I. Lathering Cleansing Phase Composition | | | |
| Miracare SLB-365 (from Rhodia) (Sodium Trideceth Sulfate, Sodium Lauramphoacetate, Cocamide MEA) | 47.4 | 47.4 | 47.4 |
| Cocamide MEA | 3.0 | 3.0 | 3.0 |
| Guar Hydroxypropyltrimonium Chloride (N-Hance 3196 from Aqualon) | 0.7 | 0.7 | 0.7 |
| PEG 90M (Polyox WSR 301 from Dow Chemical) | 0.2 | 0.2 | 0.2 |
| Glycerin | 0.8 | 0.8 | 0.8 |
| Sodium Chloride | 3.5 | 3.5 | 3.5 |
| Disodium EDTA | 0.05 | 0.05 | 0.05 |
| Glydant | 0.67 | 0.67 | 0.67 |
| Citric Acid | 0.4 | 0.4 | 0.4 |
| Perfume | 2.0 | 2.0 | 2.0 |
| Red 7 Ca Lake (From LCW) | 0.01 | 0.01 | 0.01 |
| Water | Q.S. | Q.S. | Q.S. |
| (pH) | (6.0) | (6.0) | (6.0) |
| II. Non-Lathering Structured Aqueous Phase Composition | | | |
| Acrylates/Vinyl Isodecanoate Crosspolymer (Stabylen 30 from 3V) | 1.0 | 1.0 | 1.0 |
| Xanthan gum (Keltrol CGT from CP Kelco) | 1.0 | 1.0 | 1.0 |
| Superwhite Protopet | 10 | 20 | 40 |
| Triethanolamine | 1.5 | 1.5 | 1.5 |
| Sodium Chloride | 3.5 | 3.5 | 3.5 |
| Glydant | 0.37 | 0.37 | 0.37 |
| Water and Minors | Q.S. | Q.S. | Q.S. |
| (pH) | (6.0) | (6.0) | (6.0) |

The compositions described above can be prepared by conventional formulation and mixing techniques. The lathering cleansing phase composition can be prepared by forming the following premixes: adding citric acid into water at 1:1 ratio to form a citric acid premix, add polyox WSR-301 into glycerin at 1:3 ratio to form a polyox-glycerin premix, and add cosmetic pigment into glycerin at 1:20 ratio to form a pigment-glycerin premix and mix well using a high shear mixer. Then, add the following ingredient in the main mixing vessel in the following sequence: water, N-Hance 3196, polyox premix, citric acid premix, disodium EDTA, and Miracare SLB-365. Mix for 30 mins, then begin heating the batch to 120 F. Add CMEA and mix until homogeneous. Then, cool the batch to ambient temperature and add the following ingredients: sodium chloride, glydant, cosmetic pigment premix and perfume. Mix the batch for 60 mins. Check pH and adjust pH using citric acid or caustic solution if needed.

The non-lathering structured aqueous phase can be prepared by slowly adding Stabylene 30 into water with continuous mixing. Then, add Keltrol CG-T. Heat the batch to 85 C with continuous agitation. Then, add Superwhite Protopet. Cool down the batch to ambient temperature. Then, add Triethanolamine. The batch becomes viscous. Add sodium chloride, glydant and mix until homogeneous.

Examples 19-22

The following examples described in Table 7 are non-limiting examples of lathering cleansing phase and non-lathering structured aqueous phase compositions of the present invention.

TABLE 7

Lathering Cleansing Phase and Non-Lathering Structured Aqueous Phase Compositions

| Ingredient | Example 19 wt % | Example 20 wt % | Example 21 wt % | Example 22 wt % |
|---|---|---|---|---|
| I. Lathering Cleansing Phase Composition | | | | |
| Sodium Lauryl Sulfate | — | — | 7.7 | — |
| Sodium Trideceth Sulfate (Cedapol TD-407 from Stepan) | 15.4 | 15.4 | 7.7 | 15.4 |
| Sodium Lauroamphoacetate (Miranol L-32 Ultra from Rhodia) | 4.6 | 4.6 | 4.6 | 4.6 |
| Guar Hydroxypropyltrimonium Chloride (N-Hance 3196 from Aqualon) | 0.7 | 0.7 | 0.6 | 0.7 |
| Xanthan Gum (Keltrol 1000 from Kelco) | 0.6 | 0.6 | 0.5 | 0.6 |
| Isosteareth-2 (Hetoxol IS-2 from Global 7) | 2 | 1 | 2 | 1 |
| Laureth-2 (Arlypon F) | — | 2 | — | 2 |
| Sodium Chloride | 4.25 | 4.25 | 4.25 | 4.25 |
| Sodium Benzoate | 0.2 | 0.2 | 0.2 | 0.2 |
| Disodium EDTA | 0.13 | 0.13 | 0.13 | 0.13 |
| Glydant | 0.37 | 0.37 | 0.37 | 0.37 |
| Citric Acid | 0.8 | 0.8 | 0.8 | 0.8 |
| Perfume | 2 | 2 | 2 | 2 |
| Water | Q.S. | Q.S. | Q.S. | Q.S. |
| (pH) | (5.7) | (5.7) | (5.7) | (5.7) |
| II. Non-Lathering Structured Aqueous Phase Composition | | | | |
| Acrylates/Vinyl Isodecanoate Crosspolymer (Stayblen 30 from 3V) | 1.0 | 1.0 | 2.0 | 1.0 |
| Xanthan Gum (Keltrol 1000 from Kelco) | 1 | 1 | 1 | 1 |
| Sorbitol | — | — | — | 8 |
| Triethanolamine | 0.8 | 0.8 | 1.6 | 0.8 |
| Sodium Chloride | 3 | 3 | 4 | 3 |
| Glydant | 0.37 | 0.37 | 0.37 | 0.37 |
| Colorant | 0.01 | 0.01 | 0.01 | 0.01 |
| Water and Minors | Q.S. | Q.S. | Q.S. | Q.S. |
| (pH) | (5.7) | (5.7) | (5.7) | (5.7) |

The compositions described above can be prepared by conventional formulation and mixing techniques. Add the following ingredients into the main mixing vessel in the following sequence: water, sodium lauryl sulfate, sodium trideceth sulfate, sodium lauroamphoacetate sodium chloride, sodium benzoate, disodium EDTA, Glydant and salt. Start agitation of the main mixing vessel. In a separate mixing vessel, disperse N-Hance 3196 in water at 1:10 ratio and form a polymer premix. Add the completely dispersed polymer premix into the main mixing vessel with continuous agitation. Disperse the xanthan gum in the laureth-2 and isosteareth-2 and then add to the batch. Adjust pH with the citric acid, then add the rest of the water and perfume into the batch. Keep agitation until a homogenous solution forms.

The non-lathering structured aqueous phase can be prepared by slowly adding Stayblen 30 and xanthan gum into water in a mixing vessel. Then, add sorbitol, salt and neutralize with triethanolamine. Finally add Glydant and colorant with agitation. Mix until homogeneous.

The lathering cleansing and non-lathering structured aqueous phases can be combined by first placing the separate phases in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The pattern is selected from the group consisting of striped, marbled, geometric, and mixtures thereof. The next step involves pumping the product that was mixed in the blending section via a hose into a single nozzle, then placing the nozzle into a container and filing the container with the resulting product. The stripe size is about 6 mm in width and 100 mm in length. The products remain stable at ambient for at least 180 days.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multi-phase personal cleansing article comprising a container comprising a multi-phase personal cleansing composition comprising:
    (a) a first phase comprising a lamellar lathering cleansing phase comprising a surfactant, water, and a lamellar structurant selected from the group consisting of fatty acids, fatty esters, trihydroxystearin, fatty alcohols, and mixtures thereof; and
    (b) at least one additional phase comprising a non-lathering structured aqueous phase comprising 70% or more of water and a water structurant comprising a polymeric water structurant and an associative water structurant;
    wherein the lathering cleansing phase and the non-lathering structured aqueous phase have Yield Points of at least about 0.1 Pa, and are packaged within said container in physical contact with one another, and wherein the personal cleansing composition is stable.

2. The personal cleansing article of claim 1, wherein the non-lathering structured aqueous phase is a hydrophilic gelled water phase.

3. The personal cleansing article of claim 1, wherein said non-lathering structured aqueous phase of the personal care composition produces a Flash Lather Volume of no greater than about 150 ml.

4. The personal cleansing article of claim 1, wherein the non-lathering structured aqueous phase has a consistency value of from about 10 to about 100,000 poise/(l/s).

5. The personal cleansing article of claim 1, wherein the non-lathering structured aqueous phase has a water mobility of less than about 2.5 seconds.

6. The personal cleansing article of claim 1, wherein the non-lathering structured aqueous phase has less than about 50% Correlated Haze.

7. The personal cleansing article of claim 1, wherein at least one phase is visually distinct from a second phase.

8. The personal cleansing article of claim 1, wherein the lathering cleansing phase further comprises:
  (i) at least one electrolyte; and
  (ii) at least one alkanolamide;
  wherein the lathering cleansing phase is non-Newtonian shear thinning; and
  the lathering cleansing phase has a viscosity of equal to or greater than about 3000 cps.

9. The personal cleansing article of claim 8, wherein the lathering cleansing phase comprises from about 1% to about 90% of a surfactant by weight of the lathering cleansing phase.

10. The personal cleansing article of claim 8, wherein the electrolyte comprises
  i) an anion selected from the group consisting of phosphate, chloride, sulfate, citrate, and mixtures thereof, and
  ii) a cation selected from the group consisting of sodium, ammonium, potassium, magnesium, and mixtures thereof; and wherein the electrolyte is present from about 0.1% to about 15% by weight of the lathering cleansing phase.

11. The personal cleansing article of claim 1, wherein said lathering cleansing phase produces a Total Lather Volume of at least about 400 ml.

12. The personal cleansing article of claim 1, wherein at least one phase comprises a colorant.

13. The personal cleansing article composition of claim 1, wherein said container is transparent.

14. The personal cleansing article composition of claim 1, wherein the lathering cleansing and non-lathering structured aqueous phases visually form a pattern within said container.

15. The personal cleansing article of claim 12, wherein said colorants are selected from the group consisting of organic pigments, inorganic pigments, interference pigments, lakes, natural colorants, pearlescent agents, dyes, carmines, and mixtures thereof.

16. The personal cleansing article of claim 12, wherein said colorant is UV stable.

17. A multi-phase personal cleansing article comprising a container comprising a personal cleansing composition comprising:
  (a) a lamellar lathering structured cleansing phase comprising a lamellar structurant selected from the group consisting of fatty acids, fatty esters, trihydroxystearin, fatty alcohols, and mixtures thereof, surfactant, and water; and
  (b) at least one additional phase comprising a non-lathering structured aqueous phase comprising 70% or more of water and a water structurant comprising i) a charged polymeric structurant, and ii) an associative water structurant, a water soluble polymeric structurant, or a combination thereof, and water;
  wherein the lathering structured cleansing phase and the non-lathering structured aqueous phase have Yield Points of at least about 0.1 Pa and are packaged within said container in physical contact with one another.

18. The personal cleansing article of claim 17, wherein the personal cleansing composition is stable.

19. The personal cleansing article of claim 17, wherein the non-lathering structured aqueous phase is a hydrophilic gelled water phase.

20. The personal cleansing article of claim 17, wherein the non-lathering structured aqueous phase has a consistency value of from about 10 to about 100,000 poise/(l/s).

21. The personal cleansing article of claim 17, wherein the non-lathering structured aqueous phase has a water mobility of less than about 2.5 seconds.

22. The personal cleansing article of claim 17, wherein the non-lathering structured aqueous phase has less than about 50% Correlated Haze.

23. The personal cleansing article of claim 17, wherein at least one phase is visually distinct from a second phase.

24. The personal cleansing article of claim 17, wherein the surfactant of the lathering structured cleansing phase comprises at least one anionic surfactant and the lathering structured cleansing phase further comprises at least one electrolyte and at least one alkanolamide.

25. The personal cleansing article of claim 24, wherein the electrolyte comprises i) an anion selected from the group consisting of phosphate, chloride, sulfate, citrate, and mixtures thereof, and ii) a cation selected from the group consisting of sodium, ammonium, potassium, magnesium, and mixtures thereof; and wherein the electrolyte is present from about 0.1% to about 15% by weight of the lathering structured cleansing phase.

26. The personal cleansing article composition of claim 17, wherein said container is transparent.

27. The personal cleansing article composition of claim 17, wherein the lathering structured cleansing and non-lathering structured aqueous phases visually form a pattern within said container.

28. A multi-phase personal cleansing composition, comprising a lamellar lathering cleansing phase comprising a cleansing surfactant, water, and a lamellar structurant selected from the group consisting of fatty acids, fatty esters, trihydroxystearin, fatty alcohols, and mixtures thereof; and a non-lathering structured aqueous phase comprising 60% or more water and a water structurant comprising an acrylates/vinyl isodecanoate crosspolymer, wherein both phases have a Yield Point of 0.1 Pa or greater.

29. The personal cleansing composition of claim 28, wherein the lathering cleansing phase comprises an anionic surfactant, an electrolyte, and an alkanolamide.

30. The personal cleansing composition of claim 29, wherein the non-lathering structured aqueous phase further comprises an electrolyte.

31. The personal cleansing article of claim 17, wherein the charged polymeric structurant comprises an acrylates/vinyl isodecanoate crosspolymer, an acrylates/C10-30 alkyl acrylate crosspolymer, a carbomer, an ammonium acryloyldimethyltaurate/VP copolymer, an ammonium acryloyldimethyltaurate/beheneth-25 methacrylate crosspolymer, an acrylates/ceteth-20 itaconate copolymer, a polyacrylamide, or a mixture thereof.

32. The personal cleansing article of claim 17, wherein the associative water structurant comprises a xanthan gum, a succinoglycan, a gellum gum, a pectin, an alginate, a starch, or a mixture thereof.

33. The personal cleansing article of claim 17, wherein the charged polymeric structurant comprises an acrylates/vinyl isodecanoate crosspolymer and the associative water structurant comprises a xanthan gum.

34. The personal cleansing article of claim 17, wherein the water structurant comprises the associative water structurant comprising a succinoglycan and the charged polymeric structurant comprises an acrylates/vinyl isodecanoate crosspolymer.

35. The personal cleansing article of claim 17, wherein the water structurant comprises the associative water structurant comprising a xanthan gum and the charged polymeric structurant comprises an acrylates/vinyl isodecanoate crosspolymer.

36. The personal cleansing article of claim 17, wherein the water structurant comprises the water soluble polymeric structurant comprising a hydroxypropyl starch phosphate and the charged polymeric structurant comprises an acrylates/vinyl isodecanoate crosspolymer.

37. The personal cleansing composition of claim 28, further comprising a succinoglycan, a xanthan gum, a hydroxypropyl starch phosphate, or a combination thereof.

* * * * *